(12) United States Patent
Murty et al.

(10) Patent No.: US 9,717,678 B2
(45) Date of Patent: Aug. 1, 2017

(54) DELIVERY SYSTEMS FOR IMPROVING ORAL BIOAVAILABILITY OF FENOBAM, ITS HYDRATES, AND SALTS

(71) Applicants: Santos B Murty, Lexington, KY (US); Ram B Murty, Lexington, KY (US)

(72) Inventors: Santos B Murty, Lexington, KY (US); Ram B Murty, Lexington, KY (US)

(73) Assignee: MURTY PHARMACEUTICALS, INC., Lexington, KY (US)

(*) Notice: Subject to any disclaimer, the term of this patent is extended or adjusted under 35 U.S.C. 154(b) by 0 days.

(21) Appl. No.: 13/667,806

(22) Filed: Nov. 2, 2012

(65) Prior Publication Data
US 2013/0122102 A1    May 16, 2013

Related U.S. Application Data
(60) Provisional application No. 61/556,269, filed on Nov. 6, 2011.

(51) Int. Cl.
| | | |
|---|---|---|
| *A61K 9/00* | (2006.01) | |
| *A61K 9/107* | (2006.01) | |
| *A61K 31/4168* | (2006.01) | |
| *A61K 9/48* | (2006.01) | |
| *A61K 9/20* | (2006.01) | |
| *A61K 9/28* | (2006.01) | |

(52) U.S. Cl.
CPC .......... *A61K 9/0002* (2013.01); *A61K 9/0065* (2013.01); *A61K 9/1075* (2013.01); *A61K 9/2846* (2013.01); *A61K 9/4866* (2013.01); *A61K 31/4168* (2013.01); *A61K 9/205* (2013.01)

(58) Field of Classification Search
CPC .. A61K 9/0002; A61K 9/4866; A61K 9/2846; A61K 9/0065; A61K 9/1075; A61K 31/4168; A61K 9/205
See application file for complete search history.

(56) References Cited

U.S. PATENT DOCUMENTS

2005/0142189 A1* 6/2005 Lambert et al. .............. 424/456

FOREIGN PATENT DOCUMENTS

WO    WO 2011053636 A1 *  5/2011

OTHER PUBLICATIONS

SBIR/STTR, "Development of a Solid Oral Dosage Form for Fenobam," <http://www.sbir.gov/node/361249>, published Aug. 25, 2011, p. 1-2.*

* cited by examiner

*Primary Examiner* — Tracy Vivlemore
*Assistant Examiner* — Monica Shin
(74) *Attorney, Agent, or Firm* — King & Schickli, PLLC (57) ABSTRACT

A delivery system for administration to a patient of Fenobam, its hydrates, and salts optimizes solubility and dissolution properties of Fenobam, its hydrates, and salts using either microemulsions, solid dispersions, cyclodextrin, gastroretentives, enteric coatings, and sustained delivery techniques to provide a vehicle for oral administration of these drugs.

6 Claims, 7 Drawing Sheets

DELIVERY SYSTEMS FOR IMPROVING ORAL BIOAVAILABILITY OF FENOBAM, ITS HYDRATES, AND SALTS

CROSS-REFERENCE TO RELATED APPLICATIONS

This non-provisional U.S. patent application is based on U.S. provisional Patent Application No. 61/556,269, filed on Nov. 6, 2011, the contents of which are incorporated by reference herein.

BACKGROUND OF THE INVENTION

Field of the Invention

The present invention relates in general to a delivery system to improve administration to patients of Fenobam, its hydrates, and salts thereof. More particularly, the present invention relates to delivery systems and compositions which optimize solubility and dissolution properties and, potentially avoid hepatic first-pass metabolism. The delivery systems of the present invention can be administered as an oral vehicle for the mammalian gastrointestinal tract and take the form of tablets, capsules, pulvule, powders, liquids, suspensions, sprays, etc.

Description of Related Art

Fenobam was originally developed by McNeil Laboratories® in the late 1970's as an anxiolytic agent, but was never commercially marketed due to dose-limiting side effects (Journal of Pharmacology and Experimental Therapeutics 315(2): 711-21 & Neuropharmacology 57 (2): 97-108). This drug compound belongs to the class known as 4-oxo-2-imidazolidinylidene ureas, which was patented by McNeil Laboratories® in U.S. Pat. No. 3,983,135. Despite the age of this drug, clinical and pharmacology researchers have just recently begun exploring alternative uses for Fenobam.

Figure 1:
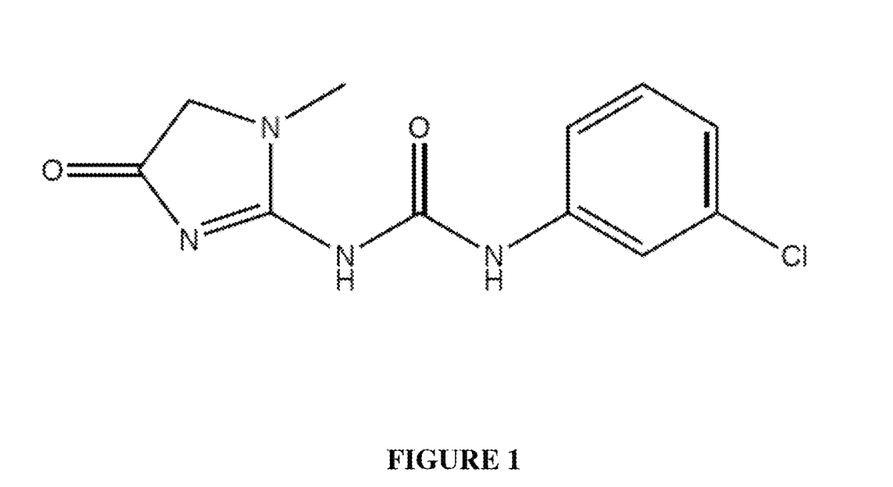
FIG. 1 illustrates the chemical structure of Fenobam.

Fenobam, having the formula $C_{11}H_{11}ClN_4O_2$, as shown in FIG. 1 below, has a molecular weight of 266.7 g/mol, and is a poorly water soluble drug compound. Equilibrium solubility data determined by applicants herein for Fenobam are shown in Table 1 below. Comparative equilibrium solubility data for Fenobam, Fenobam Monohydrate, and Fenobam Sulfate Salt are shown in Table 2 below. Further, this drug possesses a log P value of 1.863, thus indicating nominal lipophilicity.

TABLE 1

Equilibrium Solubility of Fenobam by HPLC

| Solvent | Solubility (mg/mL) |
|---|---|
| 0.1 N HCl | 0.392 |
| Acetate Buffer, pH 4.0 | 0.025 |
| Phosphate Buffer, pH 7.4 | 0.033 |
| 20% Polyethylene Glycol (PEG) 400 | 0.124 |
| Polyethylene Glycol (PEG) 400 | 24.4 |
| 20% Propylene Glycol | 0.065 |
| Propylene Glycol | 4.46 |
| 10% Polysorbate 80 | 1.19 |
| 10% Cremophor RH 40 | 0.643 |
| 30% HP-Beta-Cyclodextrin | 2.19 |
| Ethanol | 2.90 |

TABLE 2

Comparative Equilibrium Solubility by HPLC for Fenobam, Fenobam Monohydrate, & Fenobam Sulfate

| | Solubility mg/mL | | |
|---|---|---|---|
| Solvent | Fenobam (Base) | Fenobam Monohydrate | Fenobam Sulfate |
| 0.1 N HCl | 0.392 | 0.308 | 0.303 |
| Phosphate Buffer, pH 7.4 | 0.033 | 0.039 | 0.027 |
| PEG 400 | 24.4 | 34.5 | 5.65 |

Given the solubilities shown in Tables 1 and 2 above, a traditional oral drug delivery system can neither be optimized nor deemed practical for a drug such as Fenobam, and its associated hydrates and salts. A traditional oral dosage unit typically entails powder blends, which are administered directly, or filled into capsules, or compressed into tablets. Further, these powder blends typically utilize water soluble carbohydrate based ingredients for optimizing flowability and compressibility characteristics during pharmaceutical processing. Such carbohydrate ingredients can include lactose, microcrystalline cellulose, corn starch, etc.

Since Fenobam and associated hydrate and salt forms do not demonstrate sufficient aqueous solubility, especially closer to physiological pH values, an alternate or novel oral delivery system is needed for successful drug delivery to patients. The use of microemulsions, solid dispersions, cyclodextrins, gastroretentive, and sustained delivery techniques were not in use when Fenobam was first developed by McNeil Laboratories. Hence, Fenobam solubility, dissolution, and bioavailability would not be optimal utilizing conventional oral delivery systems existing at the time Fenobam was developed, such as carbohydrate based powder blends which can be administered directly, or filled into capsules, or compressed into tablets. The use of such conventional oral delivery techniques would require much higher doses of Fenobam, thus resulting in higher adverse event profiles (i.e., dose-limiting side effects).

Fenobam is a clinically validated nonbenzodiazepine anxiolytic, and is a potent mGluR5 receptor antagonist (J Pharmacol Exp Ther. 2005 November; 315 (2): 711-21). Currently, The National Institute on Drug Abuse (Bethesda, Md.) is investigating Fenobam as a potential treatment agent for cocaine addiction. Fenobam is also being investigated for the treatment of Fragile X Syndrome (J Med Genet. 46: 266-271). With these new clinical applications for this 1970's McNeil drug, an optimal clinical dosage form is now needed using new drug delivery technologies. However, traditional oral delivery systems based on carbohydrate powder blends do not achieve optimal delivery results (i.e., solubility, dissolution, bioavailability, etc.).

Accordingly, it is an object of the present invention to provide a delivery system to improve administration to patients of Fenobam, its hydrates, and salts. More particularly, an object of the present invention is to optimize solubility and dissolution properties and, in certain instances, to potentially avoid hepatic first-pass metabolism of Fenobam, thereby enhancing bioavailability through the gastrointestinal tract.

Another object of the present invention is to provide a method and composition for enhancing solubility and dissolution of Fenobam, its hydrates, and salts by employing various novel pharmaceutical compositions described hereinafter.

Yet another object of the present invention is to provide delivery systems in which administration of Fenobam, its hydrates, and salts can take place by an oral vehicle for the mammalian gastrointestinal tract, and take the form of tablets, capsules, pulvules, powder, liquids, suspensions, and sprays.

It is still another object of the present invention to provide a delivery system to improve administration to patients of Fenobam, its hydrates, and salts, and, more particularly, to provide a delivery system involving a microemulsion, and/or solid dispersion and/or, cyclodextrin, and/or gastroretentive, and/or enteric coated, and a sustained delivery technique.

It is yet another object of the present invention to provide a drug delivery system to optimize solubility and dissolution properties of Fenobam, its hydrates, and salts, and, in certain instances, potentially avoid hepatic first-pass metabolism, thereby enhancing bioavailability through the gastrointestinal tract.

Still another object of the present invention is to provide delivery systems for Fenobam, its hydrates, and salts which can be administered as an oral vehicle for the mammalian gastrointestinal tract, and take the form of tablets, capsules, pulvules, powders, liquids, suspensions, sprays.

BRIEF SUMMARY OF THE INVENTION

Applicants have conducted earnest and extensive research in an effort to meet the above described objects of the present invention. It was unexpectedly discovered during this research that new and novel approaches to the dissolution of Fenobam, its hydrates, and salts can be achieved to optimize solubility and dissolution properties by employing microemulsions, and/or solid dispersions, and/or cyclodextrins, and/or gastroretentives, and/or enteric coatings as described hereinafter.

In a first preferred embodiment, there is provided a method of a delivery system for the administration to a patient of Fenobam, its hydrates, and salts, comprising:

mixing ingredients comprising one or more of Fenobam, its hydrates, and salts with a microemulsion, comprising as an inactive ingredient low molecular weight polyethylene glycol.

In a second preferred embodiment, there is provided in connection with the first preferred embodiment a method wherein low molecular weight ingredients further comprise a hydrophilic non-ionic surfactant of a triblock copolymer consisting of a central hydrophobic block of polypropylene glycol flanked by two hydrophilic blocks of polyethylene glycol.

In a third preferred embodiment there is provided in connection with the second preferred embodiment, a method wherein the two polyethylene glycol blocks have about 101 repeating units, and the approximate length of the propylene glycol block is 56 repeating units.

In a fourth preferred embodiment, there is provided in connection with the first preferred embodiment a method wherein the inactive ingredients further comprise d-α-tocopherol polyethylene glycol 1000.

In a fifth preferred embodiment, there is provided in connection with the first preferred embodiment a method wherein the active ingredients comprise polyethylene glycols having two different molecular weight ranges, whereby to obtain a viscous solid state solution at room temperature.

In a sixth preferred embodiment, there is provided a method of a deliverable system for the administration to a patient of Fenobam, its hydrates and salts, comprising:

mixing Fenobam, its hydrates and salts with hydroxypropyl beta-cyclodextrin.

In a seventh preferred embodiment, there is provided in connection with the sixth preferred embodiment a method wherein the cyclodextrin is covalently linked sugar units in a cyclic configuration which traps and/or complexes with Fenobam, its hydrates, and salts.

In an eighth preferred embodiment, there is provided a method of providing a deliverable system for the administration to a patient of Fenobam, its hydrates, and salts, comprising:

mixing an intra-granular composition comprising Fenobam, its hydrates, and salts; citric acid anhydrous; sodium bicarbonate (heat treated); and a binder of vinyl pyrrolidone-vinyl acetate copolymer that is soluble both in water and alcohol, with an extra-granular composition comprising a cellulosic controlled release agent of hydroxypropyl methyl cellulose; magnesium stearate; and colloidal silicon dioxide.

In a ninth preferred embodiment, there is provided in connection with the eighth preferred embodiment a method wherein the intra-granular composition further comprises hydroxypropyl beta cyclodextrin.

In a tenth preferred embodiment, there is provided in connection with the ninth preferred embodiment a method wherein the extra-granular composition further comprises an enteric coating of methacrylic acid co-polymer type C or polyvinyl acetate phthalate.

In an eleventh preferred embodiment, there is provided a composition of a delivery system for the administration to a patient of Fenobam, its hydrates, and salts, comprising: ingredients of Fenobam, its hydrates, and salts with a microemulsion comprising as an inactive ingredient low molecular weight polyethylene glycol.

In a twelfth preferred embodiment, there is provided in connection with the eleventh preferred embodiment a composition wherein the low molecular weight ingredients further comprise a hydrophilic non-ionic surfactant of a triblock copolymer consisting of a central hydrophobic block of polypropylene glycol flanked by two hydrophilic blocks of polyethylene glycol.

In a thirteenth preferred embodiment, there is provided in connection with the twelfth preferred embodiment a composition wherein the two polyethylene glycol blocks have about 101 repeating units, and the approximate length of the propylene glycol block is 56 repeating units.

In a fourteenth preferred embodiment, there is provided in connection with the eleventh preferred embodiment a composition wherein inactive ingredients further comprise d-α-tocopherol polyethylene glycol 1000.

In a fifteenth preferred embodiment, there is provided in connection with the eleventh preferred embodiment a composition wherein active ingredients comprise polyethylene glycols having two different molecular weight ranges, whereby to obtain a viscous solid state solution at room temperature.

In a sixteenth preferred embodiment, there is provided a composition for a deliverable system for the administration to a patient of Fenobam, its hydrates, and salts, comprising: a mixture and/or complex of Fenobam, its hydrates, and salts with hydroxypropyl beta-cyclodextrin.

In a seventeenth preferred embodiment, there is provided in connection with the sixteenth preferred embodiment a composition wherein the cyclodextrin is covalently linked sugar units in a cyclic configuration, whereby to trap and/or complex with Fenobam, its hydrates, and salts.

In an eighteenth preferred embodiment, there is provided a composition for a deliverable system for the administration to a patient of Fenobam, its hydrates, and salts, comprising:

a mixture of an intra-granular composition comprising Fenobam, its hydrates, and salts; citric acid anhydrous; sodium bicarbonate (heat treated); and a binder of vinyl pyrrolidone-vinyl acetate copolymer that is soluble both in water and alcohol, with an extra-granular composition comprising a cellulosic controlled release agent of hydroxypropyl methyl cellulose; magnesium stearate; and colloidal silicon dioxide.

In a nineteenth preferred embodiment, there is provided in connection with the eighteenth preferred embodiment a composition wherein the intra-granular composition further comprises hydroxypropyl beta cyclodextrin.

In a twentieth preferred embodiment, there is provided in connection with the nineteenth preferred embodiment a composition wherein the extra-granular composition further comprises an enteric coating comprising methacrylic acid co-polymer type C or polyvinyl acetate phthalate.

BRIEF DESCRIPTION OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION (1) Microemulsion & Solid Dispersion Formulation Development Trials Based on the solubility data obtained for Fenobam (e.g., Table 1 & Table 2 above), initial formulation tests centered on a polyethylene glycol (PEG) based microemulsion, as well as solid dispersion formulations. With a PEG 400 solvent, as shown in Table 2 above, Fenobam demonstrated an equilibrium solubility of 24.4 mg/mL and Fenobam Monohydrate demonstrated an equilibrium solubility of 34.5 mg/mL.

PEG 400 (polyethylene glycol 400) is a low molecular weight grade of polyethylene glycol. It is a clear, colorless, viscous liquid. Due in part to its low toxicity, PEG 400 is widely used in a variety of pharmaceutical formulations. PEG 400 has a CAS number of 25322-678-3. PEG based microemulsions and solid dispersion formulations can be prepared by heating the inactive ingredients including polyethylene glycol to 60° C. (i.e., the "hot melt approach"). At this temperature, the Fenobam agents were slowly added until a clear solution was obtained. In addition, at 60° C., the formulations can be filled into hard gelatin capsules (size 00) for cooling and annealing. This PEG 400 based microemulsion formulation approach has been described for use with an FDA approved HIV treatment drug, Amprenavir (Agenerase®, U.S. Pat. No. 6,730,679).

Applicants' PEG 400 based microemulsions, however, utilize the additional polymer Poloxamer 407. Poloxamer 407 is a hydrophilic non-ionic surfactant of the more general class of copolymers known as poloxamers. Poloxamer 407 is a triblock copolymer consisting of a central hydrophobic block of polypropylene glycol flanked by two hydrophilic blocks of polyethylene glycol. The approximate lengths of the two PEG blocks is 101 repeat units while the approximate length of the propylene glycol block is 56 repeat units.

Figure 2:
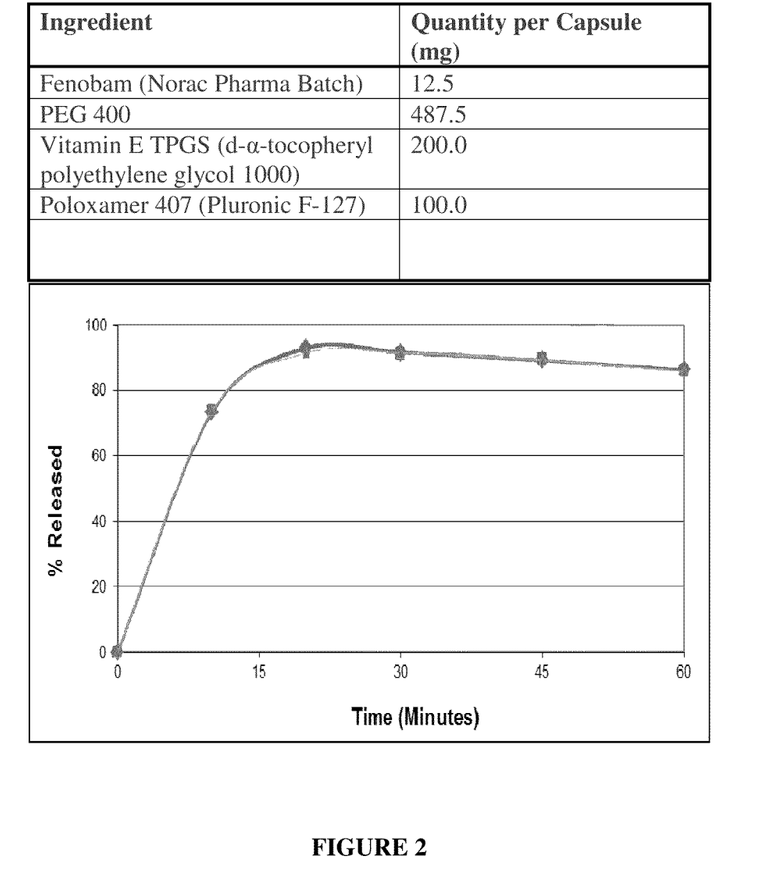
FIG. 2 is a table illustrating one embodiment of the composition of the delivery system of the present invention, with a dissolution profiled thereof.
Figure 3:
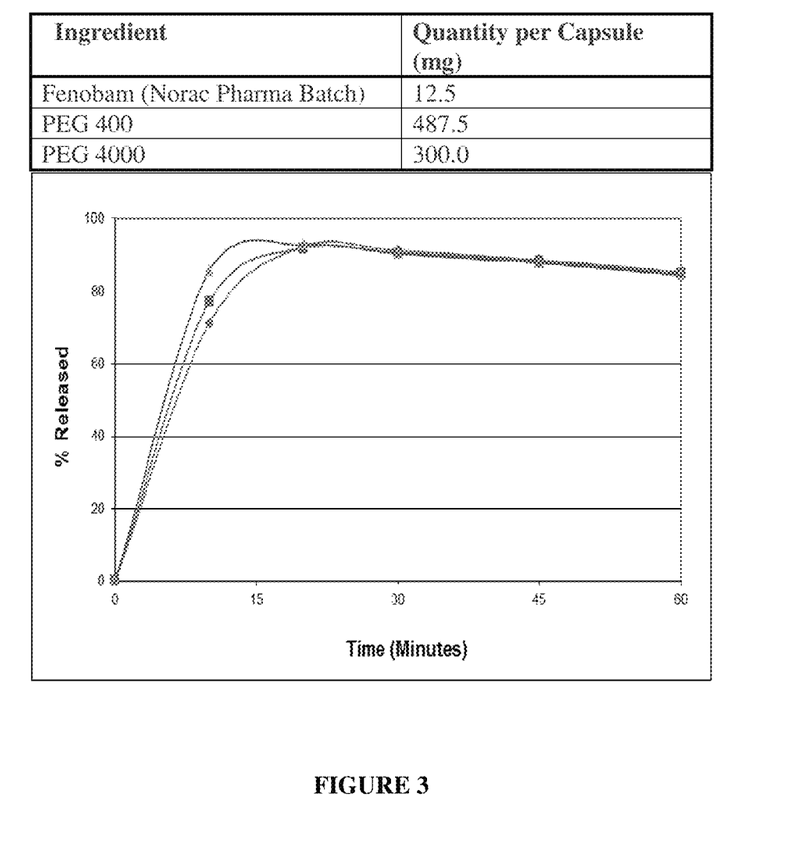
FIG. 3 is a table illustrating another embodiment of the composition of the delivery system of the present invention, with a dissolution profiled thereof.
Figure 4:
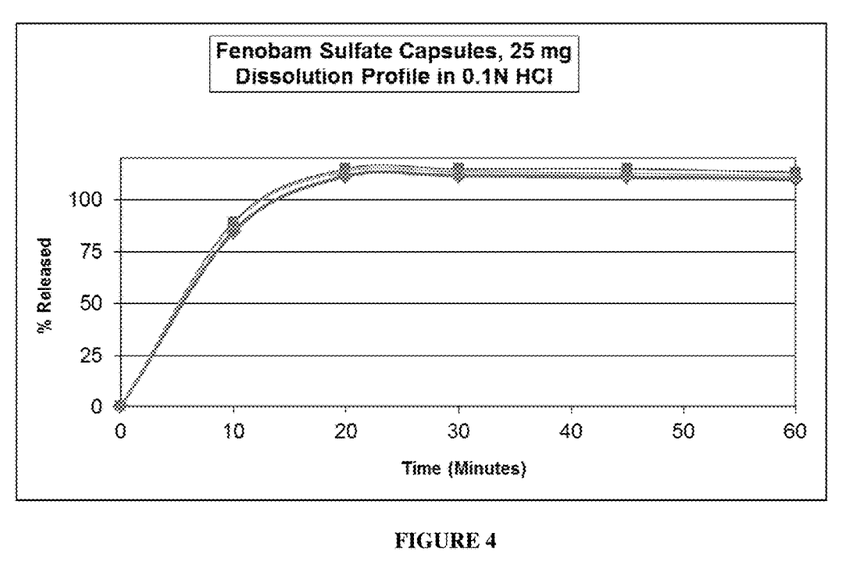
FIG. 4 is a dissolution profile for a 25 mg capsule formulation of a composition of the present invention.
Figure 5:
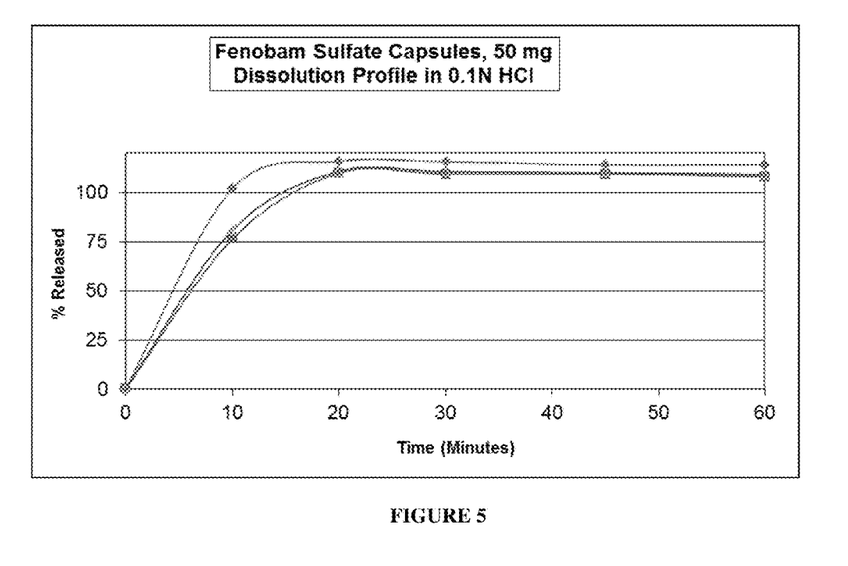
FIG. 5 is a dissolution profile for a 50 mg capsule formulation of a composition of the present invention.
Figure 6:
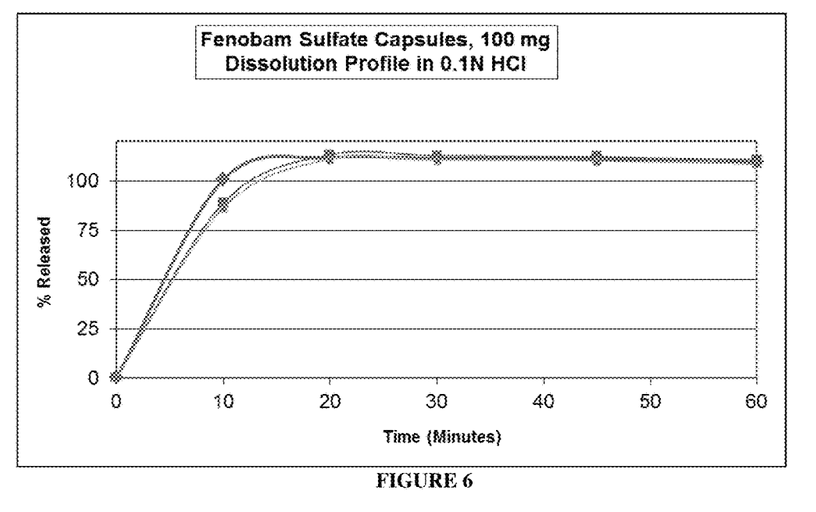
FIG. 6 is a dissolution profile for a 100 mg capsule formulation of a composition of the present invention.
Figure 7:
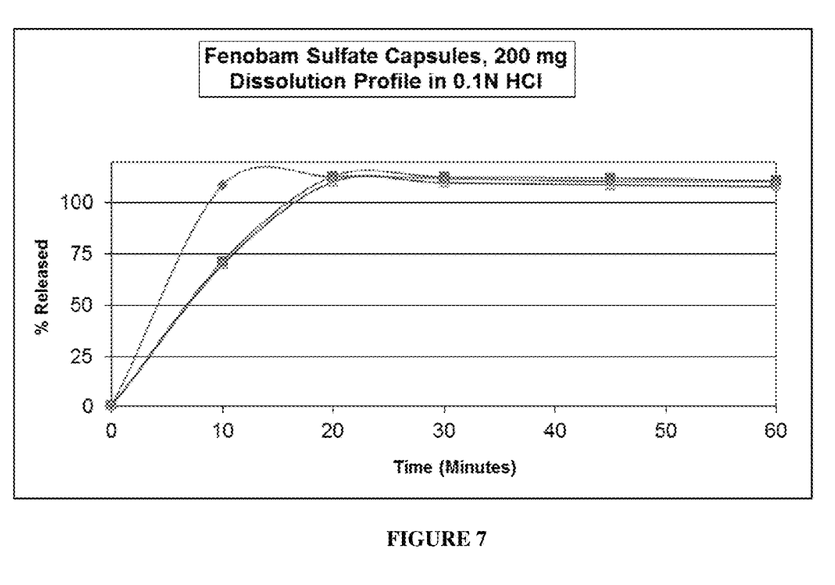
FIG. 7 is a dissolution profile for a 200 mg capsule formulation of a composition of the present invention.

Further, as an alternative to the use of microemulsions, the PEG based solid dispersion formulation rationale was employed using polyethylene glycols having two different molecular weight ranges in order to obtain a viscous solid state solution at room temperature. FIG. 2 (which includes a microemulsion dissolution profile (N=3) in 0.1 N HCl (MPI Batch # R110501)) and FIG. 3 (which includes a Fenobam solid dispersion Dissolution profile (N=3) in 0.1 N HCl (MPI Batch # R110502)) below provide the dissolution profiles from one representative composition of each formulation type (i.e., PEG microemulsions and PEG solid dispersions, respectively). Dissolution studies were performed using a USP Type II apparatus (Media: 0.1 N HCl; Paddle Speed: 100 RPM; Temperature: 37° C.).

(2) Hydroxypropyl Beta-Cyclodextrin Formulation Development Trials

Alternative to the microemulsion and solid dispersion approach as described above, cyclodextrin carrier molecules have been found to improve administration of Fenobam, its hydrates, and salts. Fenobam sulfate, for instance, unexpectedly demonstrated optimal performance when combined with hydroxypropyl beta-cyclodextrin (HPBC). An HPBC carrier system was patented by National Institutes of Health in 1984 (U.S. Pat. No. 4,727,064). Cyclodextrin carrier systems are non-traditional polysaccharides, which are covalently linked sugar units in a cyclical fashion. The resultant cyclical complex is hydrophilic on the exterior surface and hydrophobic on the internal surface. This configuration can complex with poorly water soluble drugs such as Fenobam. Hence, cyclodextrin complexes are considered atypical carbohydrate delivery systems.

Table 3 below provides a composition for capsule formulations (i.e., 25 mg, 50 mg, 100 mg, & 200 mg). The compositions described in Table 3 below were prepared by a dry mixing method. Additional methods of mixing drug and cyclodextrin complexes can involve aqueous based complexation techniques and/or wet kneading granulation techniques. Furthermore, the dissolution profiles for each capsule formulation are shown in FIGS. 4-7, respectively, for the 25 mg, 50 mg, 100 mg, & 200 mg strengths. Dissolution studies have been performed using a USP Type II apparatus (Media: 0.1 N HCl; Paddle Speed: 100 RPM; Temperature: 37° C.).

TABLE 3

Fenobam Capsule Compositions*

| Strength (as base) | 25 mg/ capsule | 50 mg/ capsule | 100 mg/ capsule | 200 mg/ capsule |
|---|---|---|---|---|
| Fenobam Sulfate | 29.6 mg | 59.2 mg | 118.4 mg | 236.8 mg |
| HPBC | 460 mg | 430 mg | 370 mg | 260 mg |
| Total | 489.6 mg | 489.2 mg | 488.4 mg | 496.8 mg |

Molecular Weight: Fenobam 266.7; Fenobam Sulfate 315.73

(3) Gastroretentive Formulation Development Trials

Alternative to the microemulsion, solid dispersion, and cyclodextrin embodiments described above, gastroretentive delivery systems have been found to improve administration of Fenobam, its hydrate, and salts. Based on the solubility data obtained in Table 1 & Table 2 above, sufficient aqueous solubility in 0.1 N HCl can be used for Fenobam, Fenobam monohydrate, and Fenobam sulfate. Hence, over a period of time, sufficient solubility exists for dissolving 100 mg of Fenobam its hydrates, and salts in 1000 mL of simulated stomach fluid (e.g., 0.1 N HCl). This discovery facilitated the design in the present invention of a gastroretentive delivery system, whereby a tablet or capsule is retained in the mammalian stomach contents over an extended period of time and does not readily pass through the pyloric sphincter with gastric emptying.

Essentially, a gastroretentive delivery system facilitates sustained release of a drug in the stomach, which takes advantage of intrinsic solubility within acidic pH for Fenobam, its hydrates, and salts. The gastroretentive effervescent delivery system, for instance, can consist of an intra-granular mix and an extra-granular mix which can be combined into a single blend (see Table 4 for compositions). This blend can then be compressed into tablets using a rotary tablet press.

Alternatively, without combining into a single blend, the intra-granular blend and extra-granular blends can be compressed separately into bi-layer tablets. Further, without using a compression machine, the intra-granular blend can be filled into a mini hard gelatin capsule (e.g., Size 2) and can be inserted into a larger sized hard gelatin capsule (e.g., Size 00) along with the extra-granular blend.

TABLE 4

Gastroretentive Effervescent Formulation

| Ingredient | Quantity/Unit (mg) | Total Quantities per Unit (mg) |
|---|---|---|
| Intra-granular Composition | | Total Intra-granular |
| Fenobam Base | 50.0 | Blend: 355.0 mg |
| Citric Acid Anhyrous | 100.0 | |
| Sodium Bicarbonate (Heat Treated) | 195.0 | |
| Kollidon VA 64 ® | 10.0 | |
| Extra-granular Composition | | Total Extra-granular |
| Methocel K4M ® | 100.0 | Blend: 108.0 mg |
| Magnesium Stearate | 4.0 | |
| Colloidal Silicon Dioxide | 4.0 | |

The functionality of the above the gastroretentive effervescent formulations can be further explained with respect to the intra-granular and extra-granular composition. Upon administration of the above formulation in the mammalian gastric fluids, the extra-granular composition swells with the absorption of aqueous fluids present in the stomach. Upon transport of aqueous fluids from the extra-granular composition to the intragranular composition, $CO_2$ gas is generated by the effervescent components of citric acid anhydrous and sodium bicarbonate. In effect, the formulation can retain buoyancy in the stomach, thereby avoiding gastric emptying through the pyloric sphincter.

In another preferred embodiment, as an additional element for the gastroretentive formulation, hydroxypropyl beta-cyclodextrin (HPBC) can be added in the intra-granular composition for solubility enhancement of Fenobam, its hydrates, and salts. Table 5 describes the compositions for the gastroretentive delivery formulation containing HPBC.

TABLE 5

Gastroretentive Effervescent Formulation with Hydroxypropyl Beta-Cyclodextrin (HPBC)

| Ingredient | Quantity/Unit (mg) | Total Quantities per Unit (mg) |
|---|---|---|
| Intra-granular Composition | | Total Intra-granular |
| Fenobam Sulfate* | 59.2 | Blend 624.2 mg |
| HPBC | 260.0 | |
| Citric Acid Anhyrous | 100.0 | |
| Sodium Bicarbonate (Heat Treated) | 195.0 | |
| Kollidon VA 64 ® | 10.0 | |
| Extra-granular Composition | | Total Extra-granular |
| Methocel K4M ® | 100.0 | Blend: 108.0 mg |
| Magnesium Stearate | 4.0 | |
| Colloidal Silicon Dioxide | 4.0 | |

*Molecular Weight: Fenobam 266.7; Fenobam Sulfate 315.73

(4) Enteric Coated & Sustained Release Formulation Development Trials

In another preferred embodiment, a sustained release delivery formulation can be prepared without the effervescent functionality. Removing the citric acid anhydrous and sodium bicarbonate from the intra-granular composition results in the formulation shown in Table 6 below. This composition does not generate $CO_2$ gas upon contact with aqueous fluids of the mammalian gastrointestinal tract. Thus, the formulation does not retain buoyancy in the stomach, thereby allowing gastric emptying through the pyloric sphincter within normal time frames. An enteric coating process of the same sustained release formulation of Table 6 below results in a formulation as described in Table 7 below. Preferably, enteric coating of the formulation can be performed with a spray coating process utilizing a perforated coating pan.

TABLE 6

Sustained Release Formulation with Hydroxypropyl Beta-Cyclodextrin (HPBC)

| Ingredient | Quantity/Unit (mg) | Total Quantities per Unit (mg) |
|---|---|---|
| Intraglanuar Composition | | Total Intragranular |
| Fenobam Sulfate* | 59.2 | Blend 329.2 mg |
| HPBC | 260.0 | |
| Kollidon VA 64 ® | 10.0 | |
| Extragranular Composition | | Total Extragranular |
| Methocel K4M ® | 100.0 | Blend: 108.0 mg |
| Magnesium Stearate | 4.0 | |
| Colloidal Silicon Dioxide | 4.0 | |

*Molecular Weight: Fenobam 266.7; Fenobam Sulfate 315.73

TABLE 7

Enteric Coated Sustained Release Formulation with Hydroxypropyl Beta-Cyclodextrin (HPBC)

| Ingredient | Quantity/Unit (mg) | Total Quantities per Unit (mg) |
|---|---|---|
| Intraglanuar Composition | | Total |
| Fenobam Sulfate* | 59.2 | Intragranular |
| HPBC | 260.0 | Blend |
| Kollidon VA 64 ® | 10.0 | 329.2 mg |
| Extragranular Composition | | Total |
| Methocel K4M ® | 100.0 | Extragranular |
| Magnesium Stearate | 4.0 | Blend: |
| Colloidal Silicon Dioxide | 4.0 | 108.0 mg |
| Opadry Clear 03K19229 Seal Coating | Target 5% w/w Gain | Total Weight Gain: |
| Acryl-EZE ® Aqueous Acrylic Enteric System with Triethyl Citrate | Target 10 % w/w Gain | 66.0 mg |

Molecular Weight: Fenobam 266.7; Fenobam Sulfate 315.73

The sustained release delivery systems described above consist of both intra-granular extra-granular compositions to be combined into a single blend in a blending operation (see Tables 6-7 above for compositions). This blend can then be compressed into tablets using a rotary tablet press. Alternatively, without combining into a single blend, the intra-granular blend and extra-granular blends can be compressed separately into bi-layer tablets. For enteric protection, tablets can be coated as described in Table 7 above.

In another preferred embodiment, without using a compression machine, the intra-granular blend can be filled into an inner mini hard gelatin capsule (e.g., Size 2) which can be inserted into an outer, larger sized hard gelatin capsule (e.g., Size 00) along with the extra-granular blend. For enteric protection, the outer and larger sized hard gelatin capsules can be selected as DRcaps® Gastro-resistant Capsules.

In the microemulsion delivery embodiment, applicants unexpectedly discovered that a co-solvent PEG 400 with a surfactant (Vitamin E TPGS) with a precipitation inhibiting polymer such as Poloxamer 407 can be used to administer Fenobam base, its hydrates, and salts. For the solid dispersion embodiment, applicants also unexpectedly discovered that utilizing a low molecular weight and higher molecular weight polyethylene glycols (PEG's) produces a solid dispersion or solid solution.

In a preferred embodiment, the microemulsion delivery approach can be used. The "Range of Options" and "Preferred Values" for this preferred approach are as follows:

a) Drug Substance (e.g., Fenobam and its hydrate forms, such as Fenobam monohydrate, and salt forms such as Fenobam sulfate): 1% to 50% w/w b) Co-Solvent (e.g., PEG 400): 1% to 99% w/w c) Surfactant (e.g., Vitamin E TPGS): 1% to 99% w/w d) Precipitation Inhibitor (e.g., Poloxamer 407): 1% to 50% w/w In another preferred embodiment using the solid dispersion delivery embodiment, the "Range of Options" and "Preferred Values" are as follows:

a) Drug Substance (e.g., Fenobam, hydrate forms like Fenobam monohydrate, and a forms like Fenobam sulfate): 1% to 50% w/w b) Low Molecular Weight Polyethylene Glycol (e.g., PEG 400): 1% to 99% w/w c) Higher Molecular Weight Polyethylene Glycol (e.g., PEG 8000): 1% to 99% w/w In yet another preferred embodiment involving the cyclodextrin delivery embodiment, applicants unexpectedly discovered that the use of a carrier complexing agent such as hydroxypropyl beta-cyclodextrin for delivering drug substances such as Fenobam, hydrate forms like Fenobam monohydrate, and salt forms like Fenobam sulfate, produces a composition which can be administered. Only certain drug molecules based on structural chemistry are suitable candidates for cyclodextrin carrier complexing agents. With the cyclodextrin delivery embodiment, the "Range of Options" and "Preferred Values" are as follows:

a) Drug Substance (e.g., Fenobam Base, hydrate forms such as Fenobam monohydrate, and salt forms such as Fenobam sulfate): 1% to 50% w/w; and b) Carrier Complexing Agent (e.g., Hydroxypropyl Beta-Cyclodextrin): 1% to 99% w/w.

In yet another preferred embodiment involving the gastroretentive effervescent delivery embodiment, applicants unexpectedly discovered that incorporation of a $CO_2$ gas generating system within the intra-granular composition with and without a carrier complexing agent such as hydroxypropyl beta-cyclodextrin (i.e., HPBC) produces a composition which can be successfully administered. Further, the $CO_2$ gas generating system within the intra-granular composition allows for buoyancy upon aqueous medium transfer from the extra-granular composition containing a hydrophilic swellable polymer such as hydroxypropyl methyl cellulose (i.e., Methocel K4M®).

Methocel® products are available in two basic types: methylcellulose and hydroxypropyl methylcellulose. Both types of Methocel® have the polymeric backbone of cellulose, a natural carbohydrate that contains a basic repeating structure of anhydroglucose units. During the manufacture of cellulose ethers, cellulose fibers are treated with caustic solution, which in turn is treated with methyl chloride and/or propylene oxide. The fibrous reaction product is purified and ground to a fine powder.

With the gastroretentive effervescent delivery embodiment, the "Range of Options" and "Preferred Values" are as follows:

i) Intra-Granular Composition (%'s Below are Based on 100% of Intra-Granular Total Composition)

a) Intra-Granular Drug Substance (e.g., Fenobam base, hydrate forms such as Fenobam monohydrate, and salt forms such as Fenobam sulfate): 1% to 50% w/w;

b) Intra-Granular Carrier Complexing Agent (e.g., Hydroxypropyl Beta-Cyclodextrin): 1% to 99% w/w;

c) Intra-Granular Effervescent System or $CO_2$ Producing System (e.g., Citric Acid Anhydrous & Sodium Bicarbonate): 1% to 99% w/w; and d) Intra-Granular Dry Binder (e.g., Kollidon VA 64®): 1% to 50% w/w. This BASF® product is a vinylpyrrolidone-vinyl acetate copolymer that is soluble in both water and alcohol.

Extra-Granular Composition (%'s Below are Based on 100% of Extra-Granular Total Composition)

a) Extra-Granular Swellable Polymer (e.g. Methocel K4M®): 1% to 99% w/w;

b) Extra-Granular Lubricant (e.g., Magnesium Stearate): 1% to 25% w/w; and c) Extra-Granular Glidant (e.g., Colloidal Silicon Dioxide): 1% 25% w/w.

In still another preferred embodiment involving the enteric coated and sustained release delivery embodiment, applicants unexpectedly discovered that an intra-granular composition with a carrier complexing agent such as hydroxypropyl beta-cyclodextrin (i.e., HPBC) can be used to produce a composition which can be administered. Further, applicants unexpectedly discovered that utilizing an enteric coating approach prevents immediate aqueous medium transfer from the extra-granular composition containing a hydrophilic swellable polymer such as hydroxypropyl methyl cellulose (i.e., Methocel K4M®). In the enteric coated and sustained release delivery embodiment, the "Range of Options" and "Preferred Values" are as follows:

Intra-Granular Composition (%'s below based 100% of Intra-Granular Total Composition):

a) Intra-Granular Drug Substance (e.g., Fenobam base, hydrate forms such as Fenobam monohydrate, and salt forms such as Fenobam sulfate): 1% to 50% w/w;

b) Intra-Granular Carrier Complexing Agent (e.g., Hydroxypropyl Beta-Cyclodextrin): 1% to 99% w/w; and c) Intra-Granular Dry Binder (e.g., Kollidon VA 64®): 1% to 50% w/w Extra-Granular Composition (%'s Below are Based on 100% of Extra-Granular Total Composition)

a) Extra-Granular Water Swellable Polymer (e.g. Methocel K4M®): 1% to 99% w/w;

b) Extra-Granular Lubricant (e.g., Magnesium Stearate): 1% to 25% w/w; and c) Extra-Granular Glidant (e.g., Colloidal Silicon Dioxide): 1% 25% w/w.

Optional Enteric Coating (%'s Below Based on Weight Gain Off of 100% of Total Intra-Granular and Extra-Granular Compositions)

a) Seal Coating (e.g., Opadry® Clear 03K19229): Target 5.0% w/w Weight Gain; and b) Enteric Coating (e.g., Acryl-EZE® Aqueous Acrylic Enteric System with Triethyl Citrate): Target 10.0% w/w Weight Gain.

Microemulsion & Solid Dispersion Delivery Embodiment

In the preferred microemulsion delivery embodiment, the alternative "Range of Options" to produce substantially the same results are as follows:

a) Drug Substance [e.g., Fenobam base, hydrate forms such as Fenobam monohydrate, and salt forms such as Fenobam sulfate]: 1% to 50% w/w;

b) Co-Solvent [e.g., Dimethylacetamide (DMA), Dimethylsulfoxide (DMSO), Ethanol, Glycerin, N-methyl-2-pyrrolidone (NMP), PEG 300, PEG 400, Poloxamer 407, Propylene Glycol]: 1% to 99% w/w;

c) Surfactant [e.g., Polyoxyl 35 castor oil (Cremophor EL®), Polyoxyl 40 hydrogenated castor oil (Cremophor RH40®), Polyoxyl 60 hydrogenated castor oil (Cremophor RH60®), polysorbate 20 (Tween 20®), Polysorbate (Tween 80®), d-α-tocopheryl polyethylene glycol 1000 succinate (Vitamin E TPGS or TPGS®), Solutol HS 15®, Sorbitan monooleate (Span 20®), PEG 300 caprylic/capric glycerides (Softigen 767®), PEG 400 caprylic/capric glycerides (Labrasol®), PEG 300 oleic glycerides (Labrafil M-1944CS®), PEG 300 linoleic glycerides (Labrafil M-2125CS®), Polyoxyl 8 stearate (PEG 400 monostearate), Polyoxyl 40 stearate (PEG 1750 monostearate)]: 1% to 99% w/w; and d) Precipitation Inhibitor [e.g., Poloxamer 338, Poloxamer 407, Poloxamer 188, Poloxamer 237, Poloxamer 124]: 1% to 50% w/w.

In the preferred solid dispersion delivery embodiment, the alternative "Range of Options" producing substantially the same results are as follows:

a) Drug Substance [e.g., Fenobam base, hydrate forms like Fenobam monohydrate, and salt forms like Fenobam sulfate]: 1% to 50% w/w; and b) Alternative polymers for direct mixing or hot melt mixing with drug substance in combination or alone [e.g., Low molecular weight polyethylene glycol (PEG 300, PEG 400, PEG 600), Higher molecular weight polyethylene glycol (PEG 1500, PEG 4000, PEG 4500, PEG 8000, PEG 20000), Plasdone C-15®, Plasdone K29/32®, Plasdone S-630®, Polyplasdone XL®, Polyplasdone XL 10®, Povidone K17®, Povidone K29/32®, Povidone K-30®, Povidone K60®, Povidone K90®, Soluplus®]: 1% to 99% w/w.

Cyclodextrin Delivery Embodiment

In the preferred cyclodextrin delivery embodiment, the alternative "Range of Options" produces substantially the same results as follows:

a) Drug Substance [e.g., Fenobam base, hydrate forms like Fenobam monohydrate, and salt forms like Fenobam sulfate]: 1% to 50% w/w; and b) Carrier complexing agent for dry mixing, wet kneading mixing, or aqueous complexation and co-precipitation [e.g., Hydroxypropyl Beta-Cyclodextrin (HPBC), Beta-Cyclodextrin Sulfobutyl Ether, 7 Sodium Salt (SBE7-β-CD), Beta-Cyclodextrin, Gamma-Cyclodextrin, & Alpha-Cyclodextrin]: 1% to 99% w/w;

Gastroretentive Delivery Embodiment

In a preferred gastroretentive effervescent delivery embodiment, the alternative "Range of Options" produce substantially the same results as follows:

Intra-Granular Composition (%'s Below are Based on 100% of Intra-Granular Total):

a) Intra-Granular Drug Substance (e.g., Fenobam base, hydrate forms such as Fenobam monohydrate, and salt forms such as Fenobam sulfate): 1% to 50% w/w;

b) Intra-Granular Carrier Complexing Agent [e.g., Hydroxypropyl Beta-Cyclodextrin (HPBC), Beta-Cyclodextrin Sulfobutyl Ether, 7 Sodium Salt (SBE7-β-CD), Beta-Cyclodextrin, Gamma-Cyclodextrin, & Alpha-Cyclodextrin]: 1% to 99% w/w;

c) Intra-Granular Effervescent System or $CO_2$ Producing System [e.g., Citric Acid Anhydrous & Sodium Bicarbonate]: 1% to 99% w/w; and d) Intra-Granular Dry Binder [e.g., Copovidone (e.g., Kollidon®), Crospovidone, Povidone, Pregelatinized Starch, Microcrystalline Cellulose, Acacia Gum Xanthan Gum, Guar Gum, Tragacanth, Pectin]: 1% to 50% w/w.

Extra-Granular Composition (%'s Below are Based on 100% of Extra-Granular Total Composition):

a) Extra-Granular Water Swellable Polymer [e.g. Hydroxypropyl Cellulose (e.g., Klucel®), Hydroxypropyl Methylcellulose (e.g., Methocel®), Hydroxypropyl Ethylcellulose, Gelcarins®, Viscarins®, Manugel®, Manucol®, Keltone®, Kelvis®, Kelcosol®, Protanal®]: 1% to 99% w/w;

b) Extra-Granular Lubricant (e.g., Magnesium Stearate, Stearic Acid): 1% to 25% w/w; and c) Extra-Granular Glidant (e.g., Colloidal Silicon Dioxide): 1% 25% w/w.

Enteric Coated & Sustained Release Delivery Embodiment

In a preferred enteric coated sustained release delivery embodiment, the alternative "Range of Options" produces substantially the same results as follows:

Intra-Granular Composition (%'s Below are Based on 100% of Intra-Granular Total):

a) Intra-Granular Drug Substance (e.g., Fenobam Base, hydrate forms such as Fenobam monohydrate, and salt forms such as Fenobam sulfate): 1% to 50% w/w;

b) Intra-Granular Carrier Complexing Agent [e.g., Hydroxypropyl Beta-Cyclodextrin (HPBC), Beta-Cyclodextrin Sulfobutyl Ether, 7 Sodium Salt (SBE7-β-CD), Beta-Cyclodextrin, Gamma-Cyclodextrin, & Alpha-Cyclodextrin]: 1% to 99% w/w; and c) Intra-Granular Dry Binder [e.g., Copovidone (e.g., Kollidon®), Crospovidone, Povidone, Pregelatinized Starch, Microcrystalline Cellulose, Acacia Gum Xanthan Gum, Guar Gum, Tragacanth, Pectin]: 1% to 50% w/w Extra-Granular Composition (%'s Below are Based on 100% of Extra-Granular Total Composition):

a) Extra-Granular Water Swellable Polymer [e.g. Hydroxypropyl Cellulose (e.g., Klucel®), Hydroxypropyl Methylcellulose (e.g., Methocel®), Hydroxypropyl Ethylcellulose, Gelcarins®, Viscarins®, Manugel®, Manucol®, Keltone®, Kelvis®, Kelcosol®, Protanal®]: 1% to 99% w/w;

b) Extra-Granular Lubricant [e.g., Magnesium Stearate, Stearic Acid]: 1% to 25% w/w; and c) Extra-Granular Glidant [e.g., Colloidal Silicon Dioxide]: 1% 25% w/w.

Optional Enteric Coating (%'s Below are Based on Weight Gain Off of 100% of Total Intra-Granular and Extra-Granular Compositions):

a) Seal coating for tablets, as needed [e.g., Opadry® Clear 03K19229): Target 5.0% w/w Weight Gain], methacrylic acid co-polymer type C, a polyvinyl acetate phthalate polymer;

b) Enteric coating for tablets, with Triethyl Citrate, as required [e.g., Acryl-EZE® Aqueous Acrylic Enteric System, Sureteric® Aqueous Enteric Coating System, Nutrateric® Nutritional Enteric Coating System, Opadry® Enteric Coating System, Eudragit® L series, Eudragit®S series,]: Target 1%-25% w/w Weight Gain; and c) Enteric coated outer capsules for holding extra-granular compositions & inner mini capsules containing Intra-Granular Compositions [e.g., DRcaps® Gastro-Resistant Capsules, Vcaps® HPMC Capsules, Vcaps® Plus HPMC Capsules].

Although specific embodiments of the present invention have been disclosed herein, those having ordinary skill in the art will understand that changes can be made to the specific embodiments without departing from the spirit and scope of the invention. Thus, the scope of the invention is not to be restricted to the specific embodiments. Furthermore, it is intended that the appended claims cover any and all such applications, modifications, and embodiments within the scope of the present invention.

What is claimed is:

1. A method of making a microemulsion delivery system for oral administration to a patient of Fenobam, its hydrates, or salts, consisting of:

mixing (a) about 1% to 50% w/w/ of Fenobam, its hydrates, or salts; (b) about 1% to 97% w/w of one or more co-solvents, wherein the one or more co-solvents are present in sufficient quantity to completely dissolve Fenobam, its hydrates, or salts based on solubility data obtained, and wherein said one or more co-solvents are selected from the group consisting of dimethylacetamide, dimethylsulfoxide, ethanol, glycerin, n-methyl-2-pyrrolidone, PEG 300, PEG 400, poloxamer 407, and propylene glycol; (c) about 1% to 97% w/w of one or more surfactants, wherein the one or more surfactants are selected from the group consisting of polyoxyl 35 castor oil, polyoxyl 40 hydrogenated castor oil, polyoxyl 60 hydrogenated castor oil, polysorbate 20, polysorbate, d-α-tocopherol polyethylene glycol 1000 succinate, sorbitan monooleate, PEG 300 caprylic/capric glycerides, PEG 400 caprylic/capric glycerides, PEG 300 oleic glycerides, PEG 300 linoleic glycerides, polyoxyl 8 stearate (PEG 400 monostearate), and polyoxyl 40 stearate (PEG 1750 monostearate); and (d) about 1% to 50% w/w of one or more precipitation inhibitors to form a microemulsion formulation such that sufficient quantity of co-solvents are present as inactive ingredients to dissolve Fenobam, its hydrates, or salts; and filling into a hard gelatin capsule.

2. The method of claim 1, wherein the one or more co-solvents is Poloxamer 407.

3. The method of claim 1, wherein the inactive ingredients consisting of polyethylene glycols having two different molecular weight ranges, whereby to obtain a viscous solid state solution at room temperature.

4. A composition of a microemulsion delivery system for oral administration to a patient of Fenobam, its hydrates, or salts, consisting of:

(a) about 1% to 50% w/w of Fenobam, its hydrates, or salts; (b) about 1% to 97% w/w of one or more co-solvents, wherein the one or more co-solvents are present in sufficient quantity to completely dissolve Fenobam, its hydrates, or salts based on solubility data obtained, and wherein said one or more co-solvents are selected from the group consisting of dimethylacetamide, dimethylsulfoxide, ethanol, glycerin, n-methyl-2-pyrrolidone, PEG 300, PEG 400, poloxamer 407, and propylene glycol; (c) about 1% to 97% w/w of one or more surfactants, wherein the one or more surfactants are selected from the group consisting of at least one of polyoxyl 35 castor oil, polyoxyl 40 hydrogenated castor oil, polyoxyl 60 hydrogenated castor oil, polysorbate 20, polysorbate, d-α-tocopherol polyethylene glycol 1000 succinate, sorbitan monooleate, PEG 300 caprylic/capric glycerides, PEG 400 caprylic/capric glycerides, PEG 300 oleic glycerides, PEG 300 linoleic glycerides, polyoxyl 8 stearate (PEG 400 monostearate), and polyoxyl 40 stearate (PEG 1750 monostearate); and (d) about 1% to 50% w/w of one or more precipitation inhibitors, to form a microemulsion formulation such that sufficient quantity of co-solvents are present as inactive ingredients to dissolve Fenobam, its hydrates, or salts configured to fill into a hard gelatin capsule.

5. The composition of claim 4, wherein the one or more co-solvents is Poloxamer 407.

6. The composition of claim 4, wherein the inactive ingredients consisting of polyethylene glycols having two different molecular weight ranges, whereby to obtain a viscous solid state solution at room temperature.

* * * * *